(12) United States Patent
Yan

(10) Patent No.: US 6,287,277 B1
(45) Date of Patent: *Sep. 11, 2001

(54) BALLOON FORMATION BY VACUUM DEPOSITION

(75) Inventor: John Yeu Jiun Yan, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/441,147

(22) Filed: Nov. 12, 1999

Related U.S. Application Data

(63) Continuation of application No. 08/848,592, filed on Apr. 28, 1997, now Pat. No. 6,013,054.

(51) Int. Cl.[7] .................................................. A61M 29/00
(52) U.S. Cl. ........................ 604/96.01; 604/916; 606/194
(58) Field of Search .................................. 604/523, 916, 604/96.01, 101.01, 103, 103.07, 919; 606/191, 194

(56) References Cited

U.S. PATENT DOCUMENTS

| 4,248,224 | 2/1981 | Jones | 128/214 |
|---|---|---|---|
| 4,309,994 | 1/1982 | Grunwald | 128/214 |
| 4,413,989 | 11/1983 | Schjeldahl et al. | 604/96 |
| 4,456,000 | 6/1984 | Schjeldahl et al. | 128/1 D |
| 4,743,327 | 5/1988 | Dehaan et al. | 156/272.6 |
| 4,952,357 | 8/1990 | Euteneuer | 264/129 |
| 4,994,071 | 2/1991 | MacGregor | 606/194 |
| 5,613,980 | 3/1997 | Clauhan | 606/194 |
| 5,669,924 | 9/1997 | Shaknovich | 606/108 |
| 5,720,735 | 2/1998 | Dorros | 604/284 |
| 5,749,825 | 5/1998 | Fischell et al. | 600/3 |

FOREIGN PATENT DOCUMENTS

| 347 023 | 3/1989 | (EP) . |
|---|---|---|
| 97/16217 | 5/1997 | (WO) . |

*Primary Examiner*—Richard K. Seidel
*Assistant Examiner*—Cris Rodriguez
(74) *Attorney, Agent, or Firm*—Heller Ehrman White & McAuliffe

(57) ABSTRACT

The invention is directed to an inflatable member for intralumenal catheter which has been formed by vapor and/or gas cover deposition and a balloon formed by the method. Multi-furcated inflatable members can be made with essentially no pin holes and other defects.

5 Claims, 3 Drawing Sheets

BALLOON FORMATION BY VACUUM DEPOSITION

This application is a continuation of copending application Ser. No. 08/848,592, filed Apr. 28, 1997, now U.S. Pat. No. 6,013,054 which is hereby incorporated herein by reference.

BACKGROUND OF THE INVENTION

This invention is directed to the formation of inflatable members and particularly to inflatable balloons for dilatation catheters used in angioplasty procedures, commonly referred to as percutaneous transluminal coronary angioplasty (PTCA).

In a typical PTCA procedure a dilatation balloon catheter is advanced over a guidewire to a desired location within the patient's coronary anatomy where the balloon of the dilatation catheter is properly positioned within the stenosis to be dilated. The balloon is then inflated to a predetermined size with radiopaque liquid at relatively high pressures which can generally range from 4–20 atmospheres to dilate the stenosed region of the diseased artery. One or more inflations may be needed to effectively dilate the stenosis. The catheter may then be withdrawn from the stenosis or advanced further into the patient's coronary anatomy to dilate additional stenoses.

The catheters used to insert stents into a patient's blood vessel are very similar to the catheters employed for angioplasty. The stent is mounted onto the balloon of the catheter in a contracted or otherwise unexpanded state, the catheter with the stent is advanced through the patient's vasculature until the balloon and stent thereon are disposed within a desired region of the patient's vasculature, such as a coronary artery. The balloon is inflated to expand the stent into position within the desired region of the patient's blood vessel.

Presently used balloons are formed of a polymer such as polyethylene terephthalate (PET), polyethylene (PE), nylon and the like. The strength requirements for balloons whether for dilatation and stent delivery has tended to increase over the years. But it has become more difficult with conventional manufacturing procedures to form high strength balloons with thin walls of uniform thicknesses without pin holes. Typical procedures involve blowing of a tubular parison, usually within a mold having an interior surface corresponding to the desired inflated shape of the balloon.

Dilatation balloons of non-standard shapes, such as bifurcated balloons shown in U.S. Pat. No. 4,456,000, are difficult to manufacture without seams, flow lines, flash or other defects. What has been needed and heretofore unavailable is a method of forming balloons having high strength, thin walls and low incidence of pin holes and in a variety of shapes and sizes without the prior defects. The present invention satisfies these and other needs.

SUMMARY OF THE INVENTION

The present invention is directed to a method of forming a thin walled high strength balloon for dilatation, stent delivery and implacement and the like, which has little incidence of pin holes and which is without seams, flow lines, flash or other defects.

In one presently preferred embodiment of the invention, a balloon is formed by deposition of a thermoplastic polymeric material or thermoplastic elastomeric material onto a mandrel of desired shape in a vacuum or low pressure environment and preferably under cover of an inert or non-reactive gas such as argon, nitrogen and the like. The mandrel has an exterior shape which corresponds to the desired inflated shape of the balloon. One presently preferred method of depositing the polymeric material onto the mandrel is radio frequency (RF) sputtering. Another method is plasma coating. Other vacuum or vapor deposition methods may also be employed to deposit polymeric material onto a mandrel to form a balloon. Suitable polymeric materials which may be vacuum deposited onto a mandrel to form a balloon include conventional dilatation balloon materials such as polyethylene, polyvinyl chloride, polyethylene terephthalate, nylon and other polyamides and zinc and sodium ionomers (e.g. Surlyn). Balloons formed of other less conventional materials such as polypropylene, polyimide, various fluoropolymers and proprietary polymeric materials such as Parylene and Parylast which are available from Advanced Surface Technology, Inc. of Billerica, Mass., may also be made with the method of the invention. Blends of polymeric materials are also suitable for deposition. Composite balloons and other catheter parts with separate layers of different polymeric materials may also be formed by the vacuum deposition of the polymeric materials. For example, a first component such as a balloon can be formed in the manner of the invention, and then be assembled with a suitable inner tubular member and catheter shaft. After the assembly, the balloon can be first coated in the manner of the invention with a suitable material such as Parylene and then Parylast is applied to further secure the balloon to the catheter shaft.

Generally, the vacuum deposition is conducted within a chamber that has a vacuum level of about $10^{-2}$ to about $10^{-10}$ torr, preferably about $10^{-3}$ to about $10^{-6}$ Torr. The gas cover is preferably argon for RF sputtering and nitrogen for plasma deposition. Other relatively inert or otherwise non-reactive gases may likewise be employed in this regard.

The balloon of the invention can be formed with a wall thickness which is uniform and accurate. Wall thicknesses between about 0.3 to over 2 mils (0.008–0.05 mm) and typically from 0.5 to about 1.5 mils (0.013–0.038 mm) can be readily formed with variations from 0.05 to 0.3 mils (0.0013–0.008 mm), typically about 0.1 to about 0.2 mils (0.0025–0.005 mm). Moreover, the balloon is essentially pin hole free and has no seams, flow lines, flash or other defects. The method of the invention is particularly adaptable to the manufacture of balloon shapes other than conventional cylindrical working sections with tapered ends, e.g. multifurcated balloons, i.e. balloons with multiple distal portions which extend distally a angles from one another. These and other advantages of the invention will become more apparent from the following detailed description of the invention, when taken in conjunction with the accompanying exemplary drawings.

DETAILED DESCRIPTION OF THE INVENTION

Figure 1:
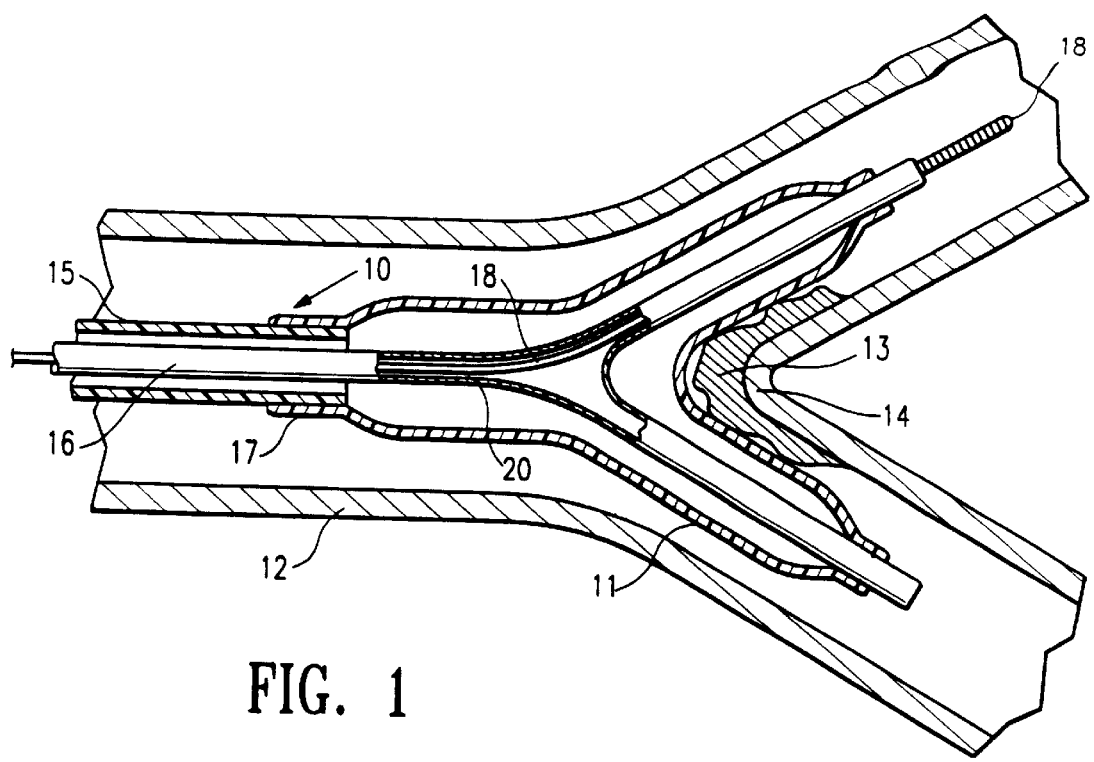
FIG. 1 is a longitudinal cross-sectional view of a dilatation catheter with a bifurcated balloon structure within a patient's blood vessel position to dilate an accumulation of plaque at an arterial branch.

Reference is made to FIG. 1 which illustrates the distal portion of a dilatation catheter 10 having a bifurcated balloon 11 within a forked branching of a patient's coronary artery 12 for dilating plaque 13 at the branch point 14 of the artery. The catheter 10 has an outer tubular member 15, a Y-shaped inner tubular member 16, a bifurcated balloon 11 having a proximal end 17 secured to the distal end of the outer tubular member 15 and distal ends of each of the bifurcated portions secured to the distal ends of the Y-shaped inner tubular member. A guidewire 18 is slidably disposed within the inner lumen 20 which extends within the inner tubular member 16.

Figure 2:
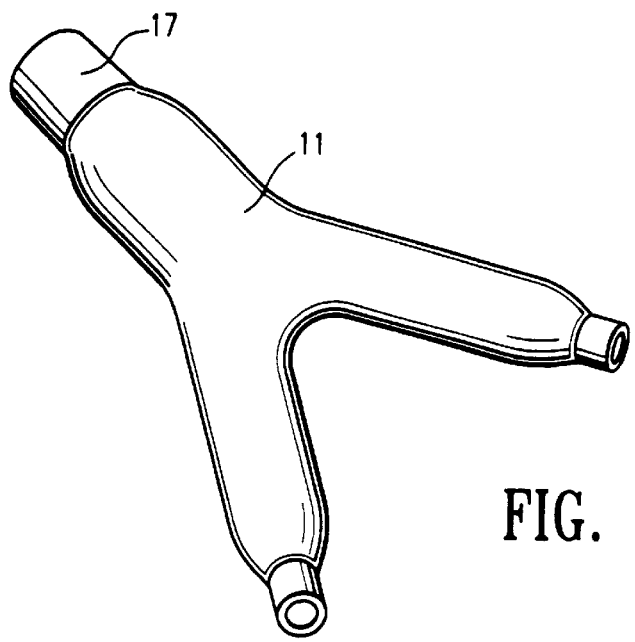
FIG. 2 is a perspective of the bifurcated balloon shown on the catheter depicted in FIG. 1.
Figure 3:
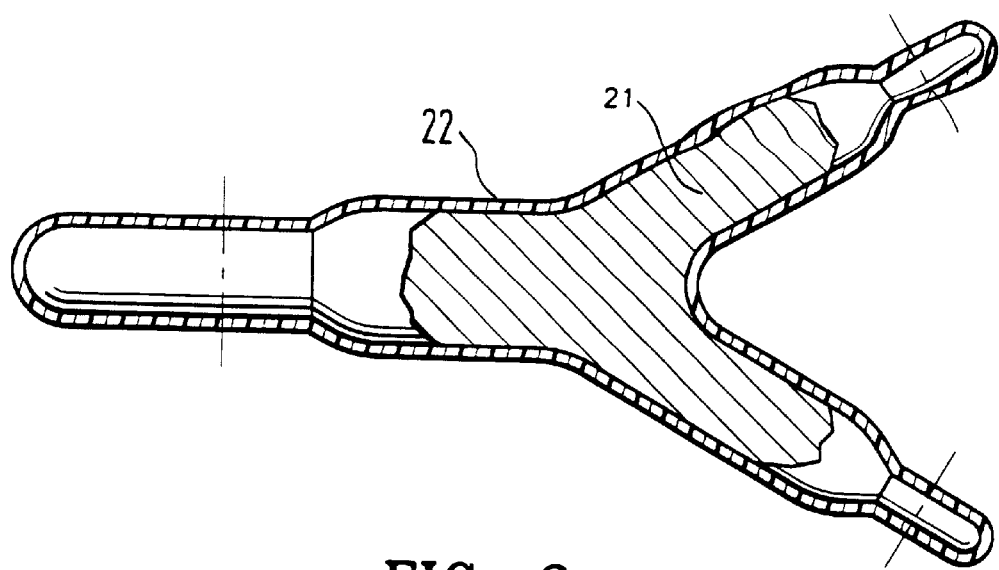
FIG. 3 is an elevational view, partially in section, of a bifurcated mandrel with a bifurcated balloon deposited thereon in accordance with the present invention.

The bifurcated balloon 11 is best illustrated in the perspective view shown in FIG. 2. FIG. 3 illustrates a bifurcated mandrel 21 onto which a layer 22 of polymeric material has been vacuum deposited to form the bifurcated balloon 11 as shown in FIG. 2.

Figure 4:
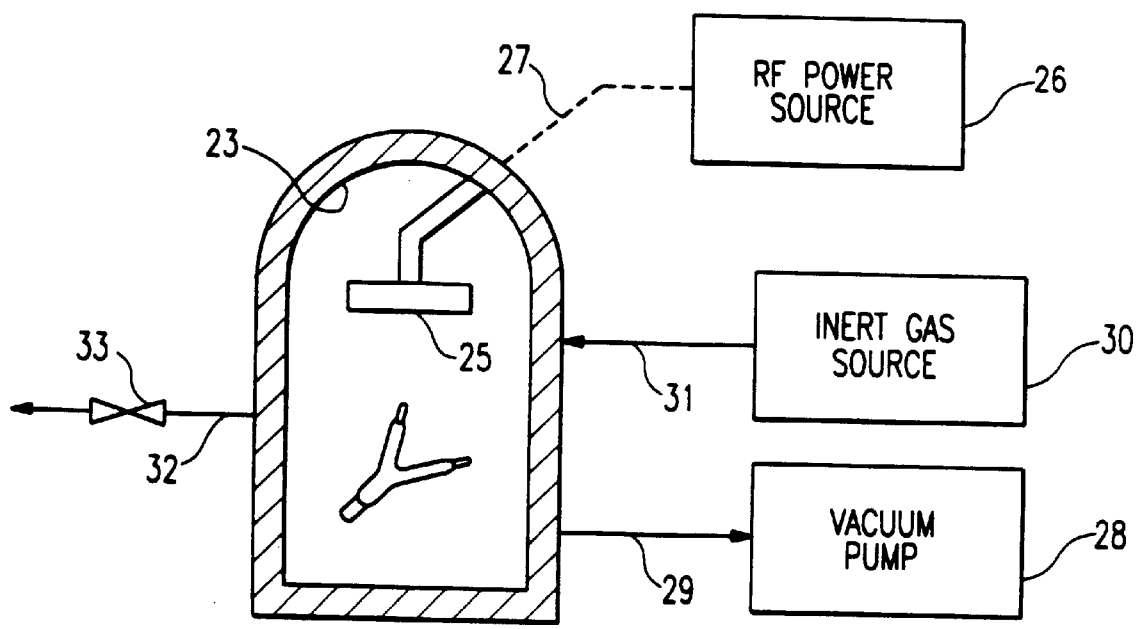
FIG. 4 is a schematic view of a system for the vacuum deposition of a polymeric layer onto a suspended mandrel to form a bifurcated balloon by RF sputtering.

FIG. 4 illustrates a system for depositing a polymer film 22 onto a bifurcated mandrel 21 as shown in FIG. 3. This system includes a vacuum chamber 23 in which the mandrel 21 is suspended. A body 25 of target material, e.g. polyethylene, is suspended within the vacuum chamber 23 and is electrically connected to a RF source 26 through cable 27. A suitable pump 28 is connected to the vacuum chamber 23 through conduit 29 to develop a vacuum within the chamber 24 at the desired levels. A source 30 of inert or non-reactive gas, e.g. argon or nitrogen, is likewise connected to the vacuum chamber 23 through a conduit 31. A vent line 32 is provided with a valve 33 to vent the chamber 23 at the end of the process.

The system shown in FIG. 4 is operated in the following manner. The mandrel 21 is suspended within the chamber 23 and the body 25 of target material is supported within the chamber electrically connected by cable 27 to an RF electrical energy source 26. The chamber 23 is closed and the pump 28 is actuated to develop a vacuum within the chamber of about $10^{-7}$ torr. An inert gas, in this case argon, is injected into the chamber 23 from the source 30 to serve as the bombardment source. After stabilization of the vacuum within the chamber 23 at a desired level of about $10^{-4}$ torr, the RF power is turned on. A plasma is generated within the chamber 23 between the polyethylene body 25 and the mandrel 21 by the ionized argon gas which bombards the polyethylene body causing dislocation of atoms and molecules of target material from the surface of the polyethylene body and the deposition thereof onto the surface of the mandrel 21. On the surface of the mandrel 21, the deposited material reacts to form a polymeric film similar to the original target material. When the desired film thickness is reached, the power to the RF source 26 is turned off. The vacuum chamber 23 is then vented through conduit 32 by opening the valve 33. When the chamber reaches atmospheric pressure, the chamber is opened and the coated mandrel 21 is removed. The mandrel 21 may be separated from the bifurcated balloon 11 formed on the surface thereof by a variety of means. For example the mandrel 21 may be made of material which is easily dissolvable by a suitable solvent which does not effect the polymeric layer on the mandrel. The proximal and distal ends of the balloon 11 are clipped to a desired length and the balloon then assembled onto the catheter shaft in a conventional manner. The balloon has a uniform thickness and no pinholes seams, flow lines, flash or other defects.

Figure 5:
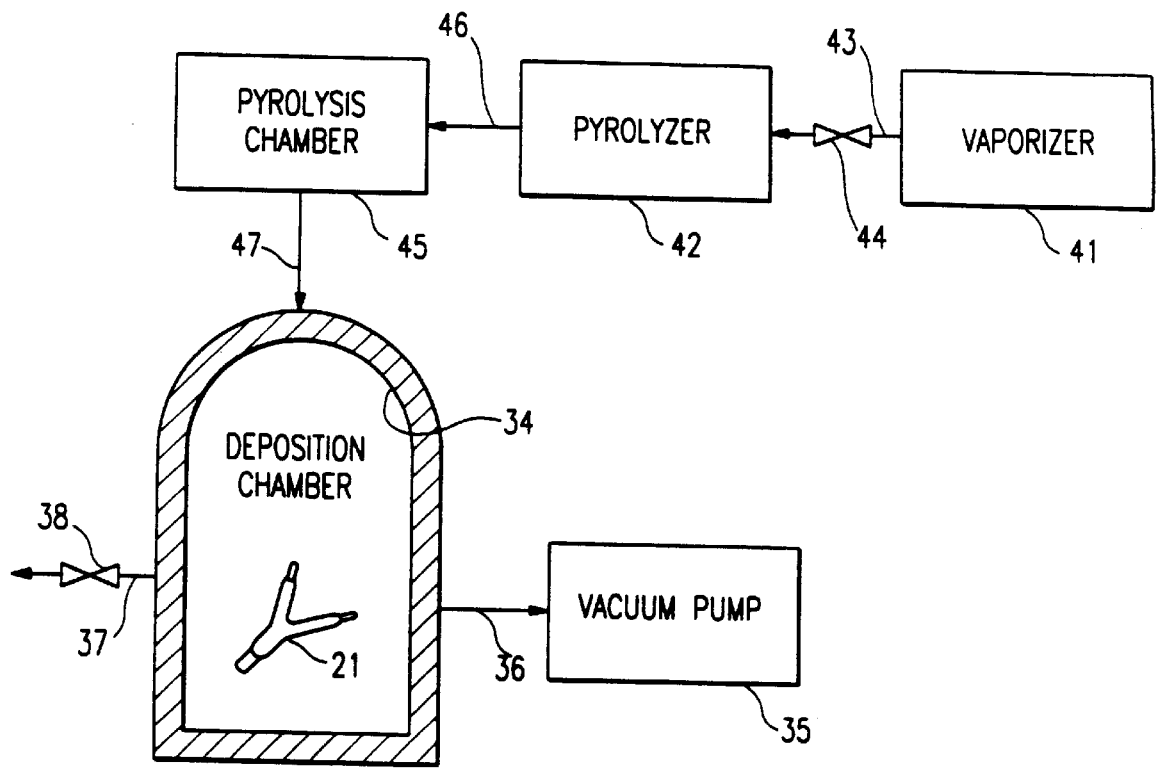
FIG. 5 is a schematic view of a system for the vacuum deposition of a polymer material onto a suspended mandrel to form a bifurcated balloon by plasma deposition.

FIG. 5 illustrates an alternative system for depositing a polymer film 22 onto a bifurcated mandrel 21 as shown in FIG. 3. This system includes a vacuum chamber 34 in which the mandrel 21 is suspended. A suitable pump 35 is connected to the vacuum chamber 34 through conduit 36 to develop a vacuum within the chamber 34 at the desired levels. A vent line 37 is provided with a valve 38 to vent the chamber 34 at the end of the process. A vaporizing vessel 41 is filled with an appropriate amount of dichloro-p-xylylene dimer. A pyrolyzer vessel 42, in fluid communication with the vaporizing vessel 41 through conduit 43, is heated to a temperature of about 700° C. When the temperature of the pyrolyzer vessel 42 is stabilized, the dimer in the vaporizer 41 is vaporized by heating the dimer to 200° C. Valve 44 in the conduit 43 is opened allowing the vaporized dimer to flow into the pyrolyzer vessel, where the dichloro-p-xylylene is heated and then into the pyrolyzer chamber 45 through conduit 46, where the dichloro-p-xylylene is cleaved into two reactive monomeric species of monochloro-p-xylylene. The reactive monomers are directed through conduit 47 to the vacuum chamber 34 which has been pumped down to a desired vacuum level of about $10^{-4}$ torr by pump 36. Within the vacuum chamber 34 the monomers polymerized at room temperature as a film of Parylene C on the surface of the mandrel 21 disposed in the chamber. When the desired polymer thickness is formed on the mandrel surface, e.g. when a fixed amount of the dimer source is depleted from the vaporizer, the vacuum chamber is vented through line 37 by opening valve 38 as in the previous example and the vacuum chamber opened so that the coated mandrel 21 can be removed. Once removed from the vacuum chamber 34, the polymer balloon 11 on the mandrel 21 can be separated in a manner as previously described.

Suitable deposition systems for the present invention include the CrC Sputtering System, particularly the CrC-150 System with a 200 watt RF power supply, available from Plasma Sciences, Inc. of Lorton, Va. and Specialty Coating System's (Indianapolis, Ind.) Parylene Coater.

Other uses may be made of the present invention. For example, the Y-shaped inner member can be made in essentially the same manner. Other alternatives include forming a Y-shaped tubular member in the manner of the invention and then irradiating the portions of the tubes which are to be blown into balloons, and the blowing the irradiated sections in a conventional manner. The method of the invention can also be employed to apply a layer of material onto a previously formed balloon so as to reap the benefits of a composite construction. Other modifications will become apparent to those skilled in the art.

Although individual features of embodiments of the invention may be shown in some of the drawings and not in others, those skilled in the art will recognize that individual features of one embodiment of the invention can be combined with any or all the features of one or more of the other embodiments. Moreover, various changes and modification can be made to the invention without departing from the scope thereof.

What is claimed is:

1. A balloon catheter comprising:
 a) an elongated shaft having proximal and distal ends, and an inflation lumen extending therein;
 b) a multifurcated balloon on a distal portion of the elongated shaft, with each of the balloon multifurcations having a distal skirt and an interior in fluid communication with the inflation lumen; and c) an inner tubular member extending within the elongated shaft having a proximal tubular portion with a first inner lumen, and a multifurcated distal tubular portion with a first branch having a second inner lumen and a second branch having a third inner lumen, both of the second and third inner lumens being in fluid communication with the first inner lumen in the proximal tubular portion, the distal tubular portion extending through the interior of the balloon multifurcations, and the first branch and the second branch having distal extremities to which the distal skirts of the multifurcated balloon are secured.

2. The balloon catheter of claim 1 wherein the multifurcated balloon is formed by deposition onto a mandrel of a desired shape.

3. A catheter, comprising an elongated shaft having proximal and distal ends, and a distal shaft section with a proximal tubular portion having an inner lumen and with a multifurcated distal tubular portion having a plurality of branches, each branch having a port in a distal end of the branch and an inner lumen in fluid communication with the port and with the inner lumen of the proximal tubular portion.

4. The catheter of claim 3 wherein the shaft comprises an outer tubular member having a lumen, and an inner tubular member having at least a section thereof disposed within the outer tubular member lumen, the inner tubular member having said distal shaft section having the proximal tubular portion and the multifurcated distal tubular portion.

5. A balloon catheter, comprising:

a) an elongated shaft having proximal and distal ends, and an inflation lumen extending therein;

b) an inner tubular member extending within the elongated shaft having a proximal tubular portion with a first inner lumen, and a multifurcated distal tubular portion with a first branch having a second inner lumen and a second branch having a third inner lumen, both of the second and third inner lumens being in fluid communication with the first inner lumen in the proximal tubular portion; and c) a first balloon section having a distal end secured to a distal end of the first branch, and a second balloon section having a distal end secured to a distal end of the second branch, the first and second balloon sections both having an interior in fluid communication with the inflation lumen, the first branch extending through the interior of the first balloon section, and the second branch extending through the interior of the second balloon section.

* * * * *